Figure 2:
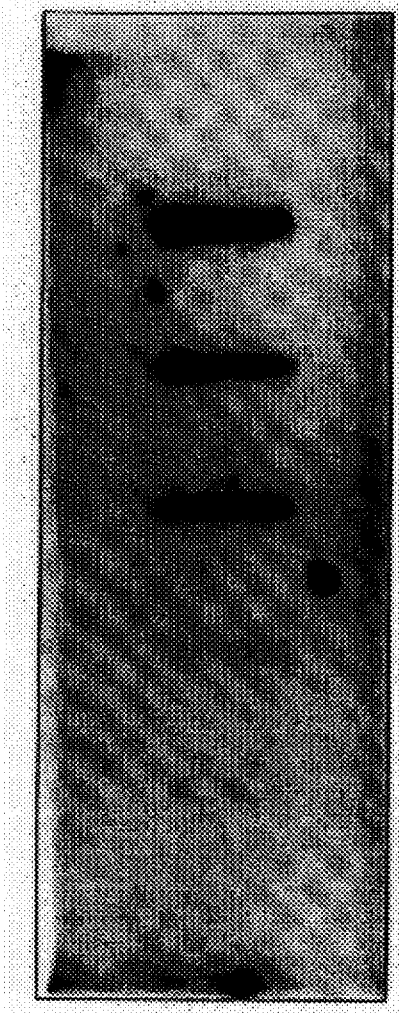

US005800985A

United States Patent [19]

Garman

[11] Patent Number: 5,800,985
[45] Date of Patent: *Sep. 1, 1998

[54] OLIGONUCLEOTIDE SIGNALLING CONJUGATE

[75] Inventor: Andrew John Garman, Ashton, England

[73] Assignee: Zeneca Limited, London, England

[*] Notice: The term of this patent shall not extend beyond the expiration date of Pat. No. 5,441,867.

[21] Appl. No.: 310,057

[22] Filed: Sep. 22, 1994

Related U.S. Application Data

[63] Continuation of Ser. No. 596,302, Oct. 15, 1990, abandoned.

[30] Foreign Application Priority Data

Oct. 13, 1989 [GB] United Kingdom ............... 8923089
Nov. 3, 1989 [GB] United Kingdom ............... 8924822

[51] Int. Cl.⁶ .................... C12Q 1/68; C07H 21/00; C07H 21/02; C07H 21/04
[52] U.S. Cl. ................... 435/6; 530/402; 530/404; 536/24.3; 536/25.32
[58] Field of Search ................. 435/6; 536/24.3, 536/25.32, 23.1; 935/77, 78; 530/402, 300, 350, 404

[56] References Cited

U.S. PATENT DOCUMENTS 5,441,867  8/1995  Garman et al. .................. 435/6

FOREIGN PATENT DOCUMENTS

| 0 173 251 A3 | 3/1986 | European Pat. Off. . |
| 0202758 | 11/1986 | European Pat. Off. . |
| 0212951 | 3/1987 | European Pat. Off. . |
| 0 304 215 A2 | 8/1987 | European Pat. Off. . |
| 0231495 | 8/1987 | European Pat. Off. . |
| 0 254 172 A2 | 1/1988 | European Pat. Off. . |
| 0 302 175 A2 | 2/1989 | European Pat. Off. . |
| 0 324 474 A1 | 7/1989 | European Pat. Off. . |
| 2192889 | 1/1988 | United Kingdom . |
| 8403520 | 9/1984 | WIPO . |
| PCT-WO89/0293 | 9/1988 | WIPO . |
| 8906701 | 7/1989 | WIPO . |

OTHER PUBLICATIONS

Guar et al, Nucl. Acids Res., V. 17, 1989, p. 4404.
Yoshitake et al, Eur. J. Biochem. V. 101 (1979) pp. 395–399.
Garman et al, Chemical Abstracts, 115:251622s.
Bischoff et al., "Introduction of 5'-Terminal Functional Groups into Synthetic Oligonucleotides for Selective Immobilization", *Analytical Biochemistry*, vol. 164, 1987, pp. 336–344.
Li et al., "Enzyme–linked synthetic oligonucleotide probes: non–radioactive detection of enterotoxigenic *Escherichia coli* in faecal specimens", *Nucleic Acids Research*, Vo. 15, No. 13, 1987, pp. 5275–5287.
Jablonski et al., "Preparation of Oligodeoxynucleotide–alkaline phosphatase conjugates and their use as hybridization probes", *Nucleic Acids Research*, vol. 14, No. 15, 1986, pp. 6115–6129.

*Primary Examiner*—Nancy Degen
*Assistant Examiner*—Thomas G. Larson
*Attorney, Agent, or Firm*—Cushman Darby & Cushman IP Group of Pillsbury Madison & Sutro, LLP

[57] ABSTRACT

Oligonucleotide signalling conjugates including a nucleic acid sequence, an amino-group containing linker group, a sulphur (thio) containing group and a non-isotopic label or marker and thiolated oligonucleotide derivative intermediates reactive with activated non-isotopic label or marker are described. The non-isotopic label is especially an enzyme such as alkaline phosphatase or horse radish peroxidase. The conjugates have application in the detection or characterisation of nucleic acid sequences and in particular in genetic characterisation.

12 Claims, 3 Drawing Sheets

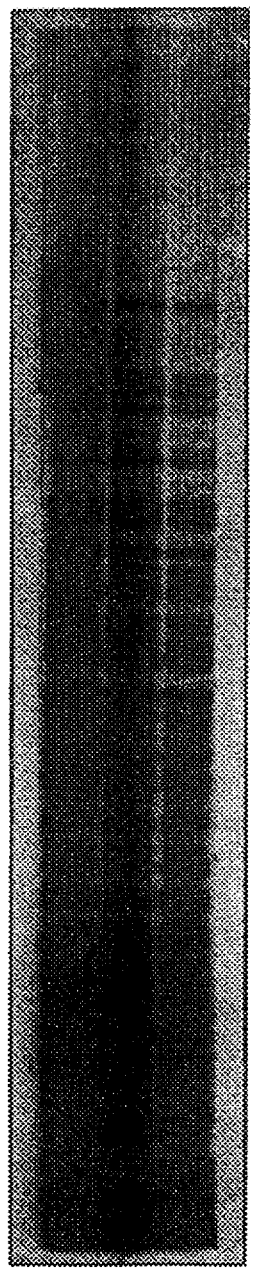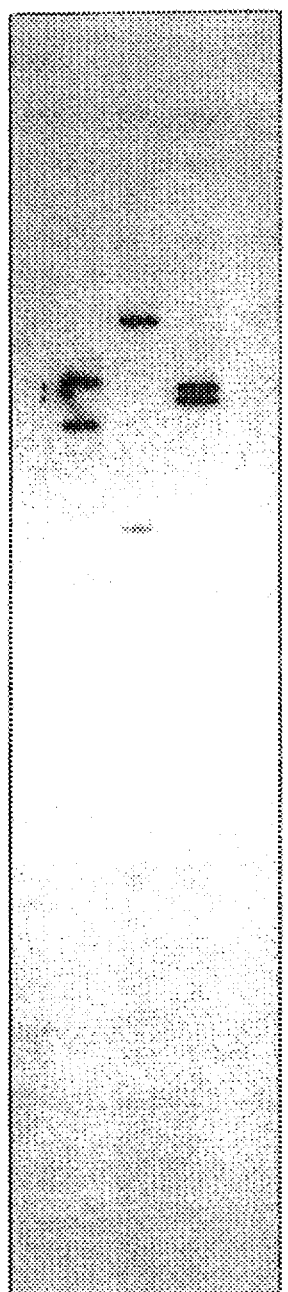

OLIGONUCLEOTIDE SIGNALLING CONJUGATE

This is a continuation of application Ser. No. 07/596,302, filed on Oct. 15, 1990, now abandoned.

The present invention relates to oligonucleotide signalling conjugates and thiolated intermediates therefor, processes for their preparation, as well as diagnostic kits comprising these. The oligonucleotide signalling conjugates of the invention are useful as hybridisation probes for the detection or measurement of nucleic acid sequences and in particular in methods of genetic characterisation.

Detection of nucleic acid sequences has hitherto mainly involved the hybridisation of a complementary nucleic acid sequence which has been radiolabelled with, for example $^{32}P$ or $^{35}S$. For reasons of safety and convenience, efforts have been made to replace these labels with non-isotopic labels such as enzymes, fluorophores and chemilumophores.

Methods for the covalent attachment of non-isotopic labels or markers to oligonucleotides have been described in the literature. These methods typically involve chemical modifications, introduced before, during or after synthesis which give rise to amino groups or thiol groups attached via a spacer arm to various parts of the oligonucleotide chain. Thus, for example Ruth et al, DNA, (1985), 4, 93 describes a uridine analogue modified at the 5' position with an extended chain terminating in an amine. Letsinger, J. A. C. S., (1981), 103, 7394 describes phosphoramidate derivatives which can be labelled via an amino function. Protected aminoalkyl phosphoramidite reagents for introducing aminoalkyl groups onto the 5' end of oligonucleotides have been described by Anserge, J. Biochem. Biophys. Methods. (1986), 13, 315–323 and Agrawal, N. A. R., (1986), 14, 6227–6245 and are now commercially available. Such amino derivatised oligonucleotides have been successfully coupled with activated fluorophores, chemilumophores and other activated molecules. However analogous coupling with proteins such as enzymes is not possible since activated derivatives of proteins able to react with amino functions cannot be readily devised or prepared.

Coupling of proteins to oligonucleotides is presently achieved by the use of thiol derivatised oligonucleotides. A protein which has been made reactive to a thiol function can then be coupled to the oligonucleotide via the thiol function. This approach is conveniently exemplified by reference to European Patent Specification No. 0202758 A (ICI).

It has been proposed to prepare an amino derivatised oligonucleotide and to react this with an amino-modifying reagent which can introduce a thiol group. This approach is described by Bischoff et al, (1987), 164, 336–344; Li et al, Nucleic Acids Research, 1987, 15, 13, 5275–5287 and R. K. Guar et al, (1989), Nucleic Acids Research, 17, 11, 4404. The methods described therein involve reaction steps less suitable for the technician requiring a convenient and straightforward method for the preparation of oligonucleotide signalling conjugates.

The present invention now provides oligonucleotide signalling conjugates which are more easily and efficiently prepared. It has also been found that for example when used as hybridisation probes the conjugates exhibit unexpectedly high signal to noise ratios between the signal due to specific hybridisation and the level of background caused by non-specific binding of the conjugate. They offer a convenient and economic alternative to conventional radiolabelled probes.

Accordingly, in a first aspect the present invention provides a conjugate of the general formula (I):

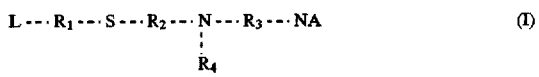

where

L is a non-isotopic label or marker moiety, NA is a nucleic acid sequence, S is sulphur, and N is nitrogen;

$R_1$ is a linking moiety derived from a thiol reactive heterobifunctional linking agent XA used to activate the non-isotopic label or marker moiety to a thiol function (in other words, effectively the agent XA is used to introduce a thiol reactive group into the label or marker in the form of a group XA'—see below);

$N(R_4)$—$R_3$ is a linking moiety derived from an amino derivative XC used to attach an amino function to the nucleic acid sequence;

R4 is hydrogen or $C_1$-$C_6$ alkyl; and

S—$R_2$ is a linking moiety derived from a thiolating agent XB used alone in a single reaction to attach a thiol function to the amino derivatised nucleic acid H—$N(R_4)$—$R_3$—NA where N, $R_4$, $R_3$ and NA are as defined above and H is hydrogen.

By the expression "used alone in a single reaction" we mean that the thiolating agent XB is solely responsible for the introduction of a thiol group and no further reagents other than for example solvent, buffer or catalyst are required.

Conjugates of the general formula I are conveniently prepared by reaction of an activated non-isotopic label or marker of the general formula (II):

where XA' is the residue of XA after reaction with the label or marker and L and XA are as defined above, with a thiolated nucleic acid of the general formula (III):

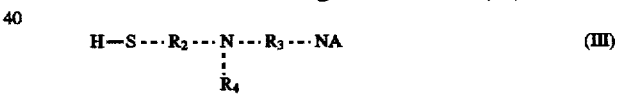

where S, H, $R_2$, N, $R_3$, $R_4$ and NA are as defined above.

The compounds of the formula (III) are novel and represent a further aspect of the present invention. They may be conveniently prepared by reaction of a thiolated derivative XB, as hereinbefore defined, with an amino derivatised nucleic acid of the general formula (IV):

where H, N, $R_3$, $R_4$, and NA are as defined above.

The thiolating agent XB used alone in a single reaction to attach a thiol function to H—$N(R_4)$—$R_3$—NA is a linking agent having a group which contains or generates a thiol group and also having a further group capable of reacting with the amino group $R_4$—NH— of the amino derivatised oligonucleotide. Thiolating reagents represented by XB include cyclic reagents with a cyclic sulphur group which react with amino functions in such a way that the ring is broken to give an SH group. Convenient reagents include homocysteine thiolactone, and, especially 2-iminothiolane:

2-iminothiolane (typically used as the hydrochloride—Traut's reagent):

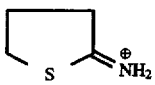

homocysteine thiolactone:

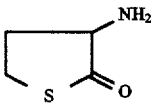

(or its N-acetylated derivative).

The length of the nucleic acid sequence represented by NA will depend on the purpose for which the oligonucleotide signalling conjugate is to be used. Where this is used as a hybridisation probe convenient lengths are up to 60, up to 50 such as 10–40, up to 40 such as 20–40, up to 30 such as 10–30, and up to 20 such as 10–20 nucleotides. The nucleic acid is conveniently DNA or RNA or analogues thereof, for example DNA, and may be present in single stranded or double stranded form. Conveniently at least the part of the nucleic acid sequence intended for hybridisation will be in single stranded form. Preferably, the nucleic acid is all present in single stranded form. Conveniently the nucleic acid sequence, for example a DNA sequence, is synthetically prepared. Methods and apparatus for such synthesis will be apparent to the scientist of ordinary skill for example using methods analogous to those described in "Oligonucleotide Synthesis, a practical approach", edited by M. J. Gait, IRL Press, Oxford (1984).

The linking moiety $R_3$ may be attached to the nucleic acid sequence at any synthetically convenient position on a sugar, base or phosphate. More conveniently it is attached to the nucleic acid sequence via the 3' or 5' terminal, for example the 3' or 5' terminal deoxyribose OH group of the nucleic acid sequence. Preferably the point of attachment is the 5' terminal OH group.

Certain amino derivatised nucleic acids of the formula (IV) are known from the references mentioned in the introduction and may for example be prepared according to the methods described therein. Other compounds of the formula (IV) may be prepared for example using analogous methods. Conveniently the compounds are prepared on a DNA synthesiser, for example on an automated, solid phase synthesiser.

Certain compounds of the formula (II) are disclosed as intermediates in European Patent Specification No 0202758 A (ICI), also by J. H. Ji in Methods Enzymol., 1983, 91, 580 and A. H. Blair et al, J. Immunol. Methods, 1983, 59, 129. The thiol reactive heterobifunctional linking agent XA used to activate the non-isotopic label or marker L to a thiol function is conveniently selected from linking agents having both a group capable of reacting with label functional groups, conveniently amino groups, and also having a further group capable of reacting with thiol groups. The latter is conveniently selected from haloacetyl, haloacetamidyl, maleimido, activated disulphide, thiols (under oxidising conditions), and heavy metal derivatives such as mercury derivatives. Such groups are conveniently joined by an optionally substituted saturated or unsaturated hydrocarbon skeleton containing for example up to 12, up to 10, up to 8, up to 6 or up to 4 carbon atoms and conveniently up to 6 carbon atoms. Examples of optional substitutents include hydroxyl groups. It will be appreciated that the chosen substituents should not interfere with the linking chemistry. Several such reagents have been described in the literature. These include reagents described in the Pierce Catalogue published by the Pierce Chemical Company. A particularly convenient reagent is the succinimidyl 4-(N-maleimidomethyl) cyclohexane-1-carboxylate (SMCC) linker as described and prepared by Yoshitake et al, European Journal of Biochemistry, (1979), 101, 395–399.

The non-isotopic label or marker component L may be a fluorophore, a chemilumophore, an enzyme or one half of a specific binding pair. The non-isotopic label or marker is conveniently proteinaceous in nature, for example enzymes, fluorescent proteins, and chemiluminescent (bioluminescent) proteins and proteins that form one half of a specific binding pair. Conjugates of the invention containing one half of a specific binding pair are not generally able to be detected directly but are conveniently incubated at a subsequent stage in the experiment or assay with the second binding partner to which is attached a signal moiety such as an enzyme, fluorophore or a chemilumophore. This approach is less preferred since it introduces an extra step, but is considered useful for some applications. Alternatively they can be premixed before hybridisation. Examples of specific binding pairs include streptavidin or avidin+biotin, antibody+hapten or protein antigen, lectin+(oligo) saccharide moiety.

Conveniently the protein is an enzyme. The present invention is particularly well suited to enzymes since the extended linkage between the enzyme and the nucleic acid sequence reduces the possibility of the enzyme interfering with hybridisation. Enzymes are used to cause a change in a substrate and this change is detected by any appropriate physical or chemical means. Convenient enzymes include peroxidases such as horse radish peroxidase (HRP), beta-galactosidase, xanthine oxidase, firefly or bacterial luciferase. A particularly convenient enzyme is alkaline phosphatase. Of course, such enzymes (or proteins forming specific binding pairs used in the invention) used in the invention can be obtained from sources in which they or their precursors occur naturally or they can be the products of recombinant technology. The enzyme is preferably in a heat stable form. Alternatively, fluorophores such as fluorescein and fluorescent lanthanide chelates or chemilumophores such as acridinium esters and luminol derivatives can be employed.

Where the enzyme alkaline phosphatase is used a particularly convenient substrate is the chemiluminescent substrate system described in European patent application, publication no. 254051 (Wayne State University), by Schaap et al, Tetrahedron Letters, 28, 11, 1155–1158 and Clin. Chem. (1989), 35, 1863–1864.

Preferred combinations of non-isotopic label or marker component L and thiol reactive heterobifunctional linking agent XA include those comprising the enzyme alkaline phosphatase and those comprising maleimido thiol reactive compounds such as the succinimidyl 4-(N-maleimidomethyl)cyclohexane-1-carboxylate (SMCC) linker.

The reaction conditions for bringing together the thiol reactive heterobifunctional linking agent XA and the non-isotopic label or marker L are preferably selected so that, on average, less than 3, for example less than 2 thiol reactive groups per molecule of L are achieved. More preferably 1–2 XA groups for example 1.4 to 1.6 conveniently 1.5 per molecule of L are achieved.

Assays may be devised by the skilled man for the measurement of the degree of modification. For example in respect of protein labels a general method involves reaction of a sample of the modified protein with an excess of a thiol compound of known concentration and measuring the amount of the, thiol compound which is left after the reaction. This method is described in Example 2 below.

The amino derivative XC used to derivatise the nucleic acid sequence to produce a compound of the formula IV is a linking agent having a group which contains or generates upon further chemical treatment an amino group R4—NH— and also having a further group capable of reacting with any convenient group on the nucleic acid sequence. Examples of convenient XC amino derivatives include those having protected amino functions. Convenient protecting groups include optionally substituted alkanoyl moieties and 9-fluorenyl methoxycarbonyl. More convenient protecting groups include halosubstituted acetyl groups such as trifluoroacetyl. The further group capable of reacting with the nucleic acid sequence conveniently comprises a phosphorous function which after reaction leaves the nucleic acid represented by NA attached to a phosphate function in the linker represented by R3. Standard phosphite chemistry for example as described in "Oligonucleotide Synthesis, a practical approach", edited by M. J. Gait (1984), IRL Press, Oxford may be employed. After coupling to the nucleic acid deprotection for example using ammonia will yield a compound of the formula IV. A convenient amino derivative XC is of the formula:

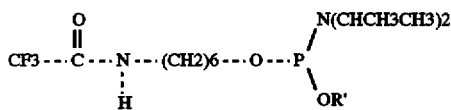

where R' is alkyl, optionally containing an electron withdrawing substituent and is e.g. methyl or 2-cyanoethyl. Where R' is methyl, the derivative is commonly referred to as amino link 2 (Applied Biosystems) and may for example be prepared using methods analogous to those disclosed in European Patent Specification No 0310312 A (Merril Lynch Technology Ventures). A further convenient amino derivative XC is of the formula:

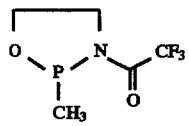

This is commonly referred to as amino link 1 (Applied Biosystems) and may be conveniently be prepared according to the methods disclosed in U.S. Pat. No. 4757141 (Applied Biosystems).

A preferred conjugate design is wherein the non-isotopic label or marker moiety is alkaline phosphatase, R1 is derived from the SMCC linker, S—R$_2$ is derived from iminothiolane, and N(R$_4$)R$_3$ is derived from amino link 2:

Appropriate packaging and instuctions for use are also optionally provided.

As outlined in the introduction the conjugates of the present invention are useful to directly replace radiolabelled hybridisation probes. They are therefore useful in a wide variety of applications such as for example, molecular biology research, clinical research, medicine, diagnosis for example of inherited disorders or infectious disease, veterinary or food science as well as agriculture.

The invention also relates to a kit comprising an oligonucleotide signalling conjugate of the general formula (I). The kit optionally includes appropriate buffer, enzyme substrate, membrane or other solid phase, packaging and instructions for use. Conveniently the conjugate is provided in a form stable for prolonged storage such as for example in lyophilised form, conveniently in the liquid form.

A particular example of their use is in methods of genetic characterisation, for example using minisatellite probes to detect VNTR regions in sample genomic DNA. These are described and claimed in UK patent No. 2166445 (Lister Institute of Preventive Medicine) and in European Patent Specification No. 0238329 A (ICI). Examples of convenient probes include the multilocus probes 33.6 and 33.15 and the single locus probes MS1, MS8, MS31, MS32, MS43, and p lambda g3 described therein.

Therefore in a further aspect of the present invention we provide a kit comprising an oligonucleotide signalling conjugate of the general formula (I) wherein the nucleic acid represented by NA is used as a hybridisation probe to detect (a) minisatellite region(s) in sample DNA. The kit optionally includes appropriate buffer, enzyme substrate, membrane or other solid phase, packaging and instructions for use. Conveniently the conjugate is provided in a form stable for prolonged storage such as for example in lyophilised form, or and preferably in liquid form.

The invention is illustrated by the following Figures and Examples. In the Figures:

FIG. 1 shows representations of the Southern Blotting bands obtained by probing sample DNA with the minisatellite probes 33.6 (UK Patent No. 2166455 Lister Institute) and MS31 (European Patent Specification No. 0238329 A).

FIG. 1(a) shows a sample of DNA from one individual (left to right 6, 4 and 2 µg) probed with a conjugate of the invention derived from minisatelite probe 33.6.

FIG. 1(b) shows samples of DNA (2 µg) from 3 individuals (lanes 1, 2 and 3 respectively) probed with a conjugate of the invention derived from minisatelite probe MS31.

FIG. 2 shows representations of the bands obtained by probing MSI DNA samples on slot blots with the oligo-

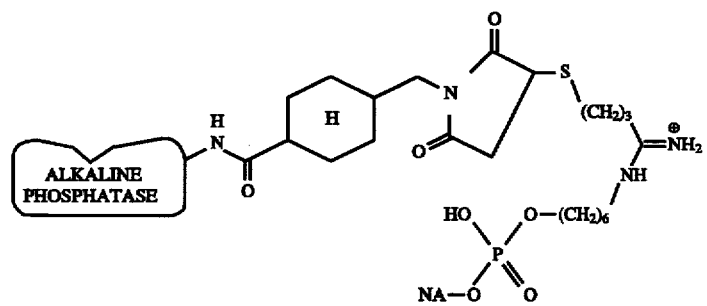

where NA is as defined in formula (I).

Means for preparing the conjugates of the present invention are conveniently provided as a kit. The kit conveniently comprises L, XA and XB optionally together with at least one of XC, nucleic acid, columns, buffers and preservatives.

nucleotide conjugate MS1 minisatellite probe prepared in Example 5. The target DNA loading was 150, 75, 30, 15, 3 and 1.5 pg in columns 1, 2, 3, 4, 5 and 6 respectively.

Figure 3:
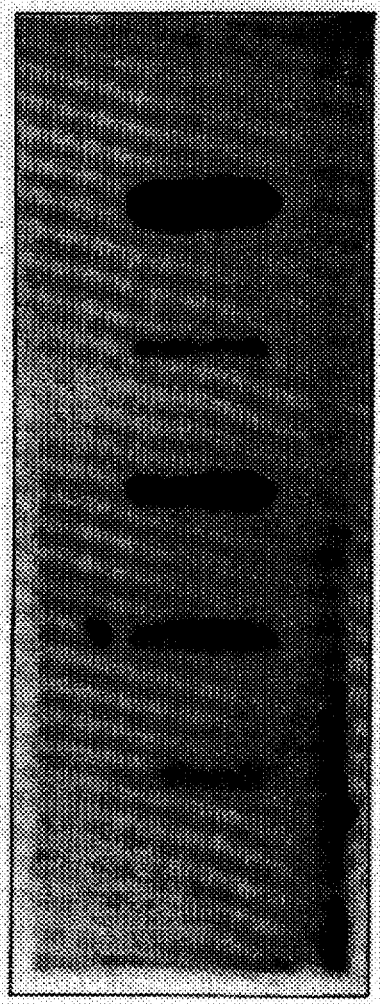

FIG. 3 shows representations of the bands obtained by probing MS1 DNA samples on slot blots with the oligo conjugate MS1 minisatellite probe prepared in Example 7. The target DNA loading was 150, 75, 30, 15, 3 and 1.5 pg in columns 1, 2, 3, 4, 5 and 6 respectively.

Figure 4:
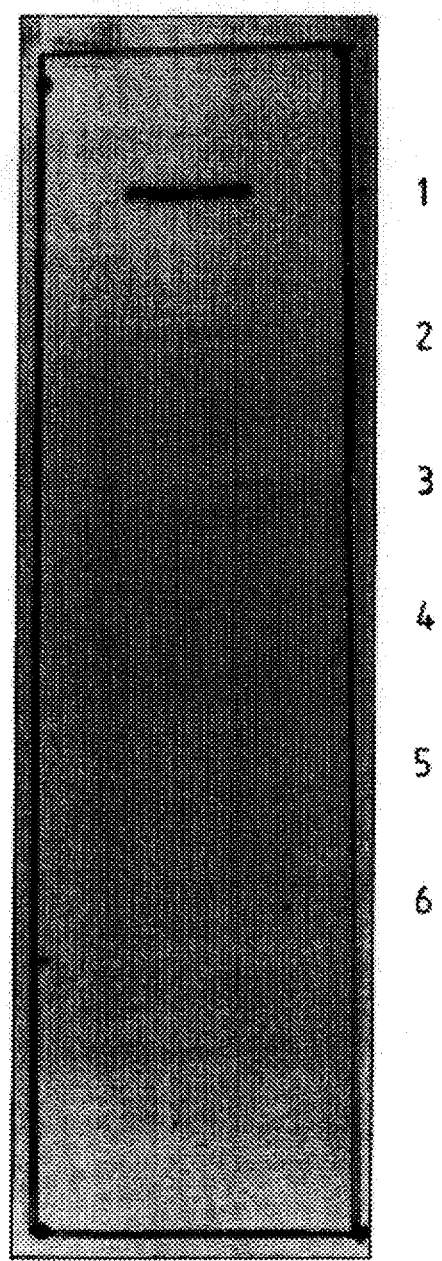

FIG. 4 shows representations of the bands obtained by probing MS1 DNA samples on slot blots with the oligo conjugate MS1 minisatellite probe prepared in Example 9. The target DNA loading was 150, 75, 30, 15, 3 and 1.5 pg in columns 1, 2, 3, 4, 5 and 6 respectively.

Example 1 describes the preparation of 5' amino derivatised oligonucleotides.

Example 2 describes the preparation of maleimido: alkaline phosphatase.

Example 3 describes the thiolation of the product of Example 1 and subsequent conjugation with the product of Example 2.

Example 4 demonstrates the efficacy of the conjugate prepared in Example 3.

Example 5 describes the thiolation of the product of Example 1 with N-acetyl homocysteine thiolactone and subsequent conjugation with the product of Example 2.

Example 6 describes the preparation of SIAB derivatised alkaline phosphatase.

Example 7 describes the thiolation of the product of Example 1 with iminothiolane and subsequent conjugation with the product of Example 6.

Example 8 describes the preparation of maleimido derivatised horse radish peroxidase.

Example 9 describes the thiolation of the product of Example 1 with iminothiolane and subsequent conjugation with the product of Example 8.

Example 10 describes the preparation of MS1 slot blots.

Example 11 describes the hybridisation of the conjugates prepared in Examples 5, 7 and 9 with slot blots prepared in Example 10.

In the Examples the following abbreviations are used:
SMCC succinimidyl 4-(N-maleimidomethyl)cyclohexane-1-carboxylate
Tris tris(hydroxymethyl)aminomethane
BSA bovine serum albumin
PBS 0.13M NaCl, 5.4 mM $Na_2HPO_4$, 1.6 mM $KH_2PO_4$ buffer pH 7.3
SSC 20x SSC is 3M NaCl, 0.3M trisodium citrate
PVP polyvinylpyrrolidone
SDS sodium dodecyl sulphate
DMF dimethyl formamide
SIAB N-Succinimidyl(4-iodoacetyl)aminobenzoate
HRP horse radish peroxidase

EXAMPLE 1

Preparation of 5' amino derivatised oligonucleotides

The following amino derivatised oligonucleotides were synthesised on a 0.2 μmol scale on an Applied Biosystems automated DNA synthesiser using protocols recommended by the manufacturer:

33.6: AL-TGGAGGAAGGGCTGGAGGAGGG

MS31: AL-TGGGAGGTGGGTAGTGTCTGTG where AL represents the linker group:

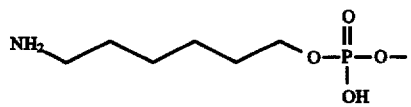

which is derived from the phosphoramidite:

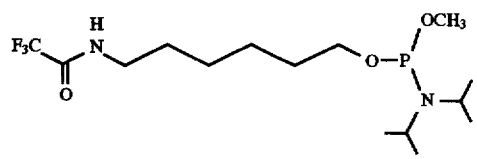

and incorporated during the solid phase synthesis. After deprotection and evaporation to dryness, the sample was redissolved in 1.0 ml of water.

EXAMPLE 2

Preparation of maleimido derivatised alkaline phosphatase

To a solution of alkaline phosphatase (Boehringer, 10 mg/ml, 0.2 ml) was added 0.1M triethanolamine HCl, 1 mM $MgCl_2$, 1 m $ZnSO_4$, pH 7.4 (0.6 ml), followed by 12 μl of a freshly prepared solution of SMCC (Pierce) in dry DMF (6.7 mg/ml) and the reaction mixture incubated at 25° C. for 30 min. The product was then purified by passage through a NAP 25 desalting column (Pharmacia), primed with BSA (Boehringer molecular biology grade) and equilibrated in PBS. The product was collected in 1.6 ml and a portion taken for analysis. Protein concentration was assessed by OD at 280 nm (using an extinction co-efficient of 0.89 for 1 mg/ml) whilst the maleimido concentration was assessed as follows: 0.15 ml of sample was reacted with 10 μl of 1 mM mercaptoethanol for 30 min. at 37° C., alongside a control with 0.15 ml of buffer alone. The reactions were then diluted with 1.2 ml of PBS, zeroed at 412 nm in a spectrophotometer, and 25 μl of 1 mM 5,5'dithio-bis(2-nitrobenzoic acid) added. Remaining thiol concentrations were thereby measured using a molar extinction coefficient of 14150, the difference between sample and control enabled the maleimido concentration and hence the degree of substitution to be calculated. This value was found to be between 1.4 and 1.6 moles maleimido per mole of protein.

EXAMPLE 3

Reaction of the 5' amino derivatised oligonucleotide with 2-iminothiolane and subsequent conjugation with alkaline phosphatase To an aqueous solution (0.2 ml) of the amino derivatised oligonucleotide (⅕th of a nominal 1 μmol synthesis) was added a freshly prepared solution (0.3 ml) of 2-iminothiolane (6 mg/ml) in 0.2M sodium bicarbonate buffer pH 9.0 and the reaction incubated at 37° C. for 30 minutes. The product was then isolated by passage through a NAP 25 desalting column (Pharmacia) equilibrated in PBS, collecting the product in 1.6 ml. This was then immediately added to the maleimido alkaline phosphatase prepared as described above. The two components were then allowed to react overnight at 4° C.

The reaction was then concentrated to ca. 0.5 ml using a BSA blocked microconcentrator (Amicon) and applied to a column (ca. 65 ml) of Biogel P-100F (Biorad) equilibrated and run in 50 mM Tris buffer pH 7.5 at a flow rate of 0.14 ml/min. The eluted peaks were detected by UV absorbance at 260 nm and UV spectra of the fractions comprising the first peak, containing the conjugate were determined. Fractions containing absorbance contributions at both 260 and 280 nm were pooled. Later fractions containing increased 280 nm contributions, believed to be free enzyme, were excluded. BSA (Boehringer, molecular biology grade) and sodium azide were added to a final concentration of 1 mg/ml and 0.2%, respectively.

EXAMPLE 4
Use of the conjugates in Southern blotting

Nylon filter Southern blots of human DNA digested with Hinf I were prepared essentially as described by A. J. Jeffreys et al, Nature, 1985, 314, 67. The filters were then pre-wetted in SSC and then rolled and placed in 30 ml universal containers. These containers were rotated in 5x SSC, 1% SDS, 0.1% BSA, 0.1% Ficol 400 (Pharmacia), 0.1% PVP 44000 (BDH) for 2 hours at 50° C. in a Bachofer oven. The conjugate was then added to the universal container to a concentration of 0.25 nM and allowed to incubate with rotation for 20 minutes at 50° C. The filters were then transferred to a box containing 1% SDS in 1x SSC, and washed in a shaking water bath for 5 minutes at 50° C. This wash step was repeated three times for the 33.6 conjugate. For MS31 there then followed a further identical wash, followed by two further wash steps in 0.25x SSC, 1% SDS. Both filters were then given a final wash in 1x SSC alone, this latter wash was carried out at room temperature. The filters were then sprayed with the chemiluminescent alkaline phosphatase Lumiphos (Lumigen Inc.), placed between transparent film in a cassette and exposed to Agfa Curix film for 1.5 hours (for 33.6) or 2 hours (for MS31).

Results for DNA from different individuals are shown in FIG. 1.

EXAMPLE 5
Reaction of the 5' amino derivatised oligonucleotide with N-acetyl homocystane thiolactone and subsequent conjugation with alkaline phosphatase.

To an aqueous solution (20 µl) of the amino derivatised oligonucleotide (⅕oth of a nominal 1 µmol synthesis) was added a freshly prepared solution (100 µl) of N-acetyl homocysteine thiolactone (6.5 mg/ml) in 0.2M sodium bicarbonate buffer pH 9.2 and the reaction incubated at 37° C. for 30 minutes. The product was then isolated by passage through a NAP 5 desalting column (PHARMACIA) equilibrated in PBS, collecting the product in 600 µl. This was immediately added to maleimido derivatised alkaline phosphatase (3 nmol) prepared as described above. The two components were then allowed to react overnight at 4° C.

The reaction was then applied to a column (ca. 10 ml) of Biogel P-100c (Biorad) equilibrated and run in 50 mM Tris buffer pH 7.5, 0.1% BSA and 0.2% sodium azide. The purified conjugate was recovered in a volume of 1.1 ml.

EXAMPLE 6
Preparation of SIAB derivatised alkaline phosphatase

To a solution of alkaline phosphatase (Boehringer, 10 mg/ml, 0.1 ml) was added 0.1M triethanolamine HCl, 1 mM MgCl$_2$, 1 mM ZnSO$_4$, pH 7.4 (0.3 ml), followed by 7 µl of a fresh prepared solution of SIAB (PIERCE) in dry DF (8.3 mg/ml) and the reaction mixture incubated at 25° C. for 30 minutes. The product was then purified by passage through a NAP 25 desalting column (PHARMACIA), primed with BSA (molecular biology grade) and equilibrated in PBS. The product was collected in 1.6 ml and immediately added to modified oligonucleotide as described in Example 7 below.

EXAMPLE 7
Reaction of the 5' amino derivatised oligonucleotide with 2-iminothiolane and subsequent conjugation with SIAB derivatised alkaline phosphatase.

To an aqueous solution (0.1 ml) of the amino derivatised oligonucleotide (⅕oth of a nominal 1 µmol synthesis) was added a freshly prepared solution (0.15 ml) of 2-iminothiolane (6.4 mg/ml) in 0.2M sodium bicarbonate buffer pH 9.2 and the reaction incubated at 37° C. for 30 minutes. The product was then isolated by passage through a NAPIO desalting column (PHARMACIA) equilibrated in PBS, collecting the product in 0.7 ml. This was then immediately added to the SIAB derivatised alkaline phosphatase prepared as described in Example 6 above. The two components were then allowed to react overnight at 4° C.

The reaction was then concentrated to ca. 1 ml using a BSA blocked microconcentrator (Amicon). Of this 0.6 ml was then applied to a column (ca. 10 ml) of Biogel P-100c (BIORAD) equilibrated and run in 50 mM Tris buffer pH 7.5, 0.1% BSA and 0.2% sodium azide. The purified conjugate was recovered in a volume of 1.1 ml.

EXAMPLE 8
Preparation of maleimido derivatised horse radish peroxidase

A sample of 2.5 mg of freeze-dried ERP (Biozyme) was weighed out and dissolved in 0.1M triethanolamine HCl, 1 mM MgCl$_2$, 1 mM ZnSO$_4$, pH 7.4 (0.8 ml). To this was added a 50 µl of a freshly prepared solution of SMCC (PIERCE) in dry DMF (17.4 mg/ml) and the reaction mixture incubated at 25° C. for 40 minutes. The product was then purified by passage through a NAP 25 desalting column (PHARMACIA) primed with BSA and equilibrated in 5 mM phosphate, 1% lactose buffer pH 7.4. The product was collected in 1.6 ml and a portion taken for analysis. Protein concentration was assessed by OD at 280 nm (using an extinction coefficient of 0.7 to 1 mg/ml) whilst the maleimido concentration was determined using the protocol described in Example 2 above.

The calculated degree of substitution was 1.43 moles maleimido per mole of protein.

EXAMPLE 9
Reaction of the 5' amino derivatised oligonucleotide with 2-iminothiolane and subsequent conjugation with maleimido derivatised horse radish peroxidase To an aqueous solution (40 µl) of the amino derivatised oligonucleotide (⅕oth of a nominal 1 µmol synthesis) was added a freshly prepared solution (60 µl) of 2-iminothiolane (16 mg/ml) in 0.66M sodium bicarbonate buffer pH 9.2 and the reaction incubated at 37° C. for 30 minutes. The product was isolated by passage through a NAP 5 desalting column (PHARMACIA) equilibrated in PBS, collecting the product in 600 µl. This was immediately added to maleimido-derivatised horse radish peroxidase (6 nmol) prepared as described in Example 8. The two components were then allowed to react overnight at 4° C.

The reaction was then applied to a column (ca. 10 mls) of Biogel P-100 (Biorad) equilibrated and run in 50 mM Tris HCl buffer pH 7.5, 0.1% BSA, 0.2% sodium azide. The purified conjugate was recovered in a volume of 1.1 ml.

EXAMPLE 10
Preparation of Slot Blots

Slot blots were made with MS1 DNA bound to Hybond-N membrane. Dilutions of MS1 were made to the following concentration (pg/µl): 30, 15, 6, 3, 0.6, 0.2.

Denaturation buffer was prepared as follows:
to 14.8 ml of water was added 1.7 ml 1M Tris HCl buffer, pH 7.5, 3 ml 2M NaOH, and 10 ml of 20 x SSC.

5 µl DNA solution was added to 295 µl denaturation buffer and the sample was incubated in a boiling water bath for 10 minutes, transferred to an ice bath and neutralised with 100 µl 1M Tris HCl pH 7.5. Slot blots were prepared using Hybond-N nylon membrane (pre-soaked in 1 x SSC), washing the slots first with 0.4 ml 1 x SSC, applying the denatured sample (0.4 ml) and washing the slots with a further 0.4 ml of 1 x SSC.

The membrane was air dried on filter paper for 20 minutes, wrapped in Soran-Wrap, uv-irradiated for 4 minutes then air dried completely.

EXAMPLE 11
Hybridisation of conjugate to Slot Blots

Slot blots were placed in sandwich boxes and incubated in hybridisation solution for 2 hours at 50° C. in a shaking water bath. The hybridisation solution was then replaced with 50 mls of fresh hybridisation solution and 50 μl of DNA probe was added. The filters were incubated in this hybridisation solution for 20 minutes at 50° C. in a shaking water bath. After hybridisation, the filters were washed twice in wash solution 1 for 5 minutes at 50° C., twice in wash solution 2 for 5 minutes at 50° C. and once in 1 x SSC for 5 minutes at ambient temperature.

Filters probed with alkaline phosphatase conjugates were placed on a plastic tray and sprayed with Lumiphos (Lumigen Inc) and then sealed between acetate sheets, incubated at 37° C. for 1 hour and exposed to X-ray film (Fuji). An initial activation period of 1 hour at 37° C. was allowed for development of the signal.

Filters probed with horse radish peroxidase conjugates were detected using ECL detection System (Amersham) and exposing filters to film at ambient temperature.

I claim:

1. A conjugate of the formula $$L-R_1-S-R_2-N(R_4)-R_3-NA \quad (I)$$

wherein

L is a non-isotopic label or marker

NA is a nucleic acid of predetermined sequence, $R_1$ and $R_3$ are hydrocarbon linkers wherein $R_1$ comprises a haloacetamidyl, maleimido or N-hydroxylsuccinimido ester group, $R_4$ is hydrogen or $C_{1-6}$ alkyl, and $R_2$ is $$-CH_2-CH_2-\overset{R}{\underset{|}{CH}}-\overset{O}{\underset{\|}{C}}-$$

wherein R is hydrogen, $-NH_2$ or $-NH-CO-CH_3$, and Q is oxygen or $NH_2+$.

2. The conjugate of claim 1 wherein said nucleic acid NA is DNA or RNA in single stranded form.

3. The conjugate of claim 1 wherein L is selected from the group consisting of a fluorophore, a chemilumophore, an enzyme, and one member of a specific binding pair.

4. The conjugate of claim 1 wherein L is an enzyme selected from the group consisting of peroxidase, a beta-galactosidase, a xanthine oxidase, a firefly luciferase and a bacterial luciferase.

5. The conjugate of claim 1 wherein L is a horse radish peroxidase.

6. The conjugate of claim 1 wherein L is alkaline phosphatase.

7. A method of making the conjugate of claim 1 comprising reacting a compound of the formula II $$L-R_1 \quad (II)$$

wherein $R_1$ and L are as defined in claim 1 with a compound of the formula III $$H-S-R_2-N(R_4)-R_3-NA \quad (III)$$

wherein $R_2$, $R_3$, $R_4$ and NA are as defined in claim 1.

8. A kit for performing nucleic acid hybridization assays comprising the oligonucleotide conjugate of claim 1 and optionally further comprising buffer, enzyme substrate, solid phase, packaging and instructions for use.

9. A nucleic acid hybridization assay comprising hybridizing the conjugate of claim 1 as a hybridization probe with a nucleic acid sample under hybridization conditions.

10. A method of genetic characterization comprising contacting the conjugate of claim 1 with a nucleic acid sample under hybridization conditions.

11. A thiolated nucleic acid of the general formula (III)

$$H-S-R_2-N(R_4)-R_3-NA \quad (III)$$

wherein

NA is a nucleic acid of predetermined sequence, $R^1$ and $R_3$ are hydrocarbon linkers wherein $R_1$ comprises a haloacetamidyl, maleimido or N-hydroxysuccinimido ester group, $R_4$ is hydrogen or $C_{1-6}$ alkyl, and $R_2$ is $$-CH_2-CH_2-\overset{R}{\underset{|}{CH}}-\overset{O}{\underset{\|}{C}}-$$

wherein R is hydrogen, $-NH_2$ or $-NH-CO-CH_3$, and Q is oxygen or $NH_2+$.

12. A conjugate of the formula:

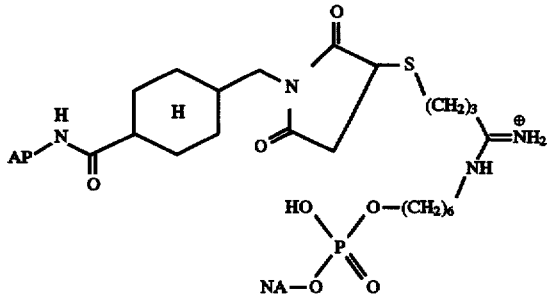

wherein NA is nucleic acid of predetermined sequence and AP is alkaline phosphatase.

* * * * *